US012790576B2

(12) United States Patent
Horner et al.

(10) Patent No.: US 12,790,576 B2
(45) Date of Patent: Nov. 10, 2026

(54) CELL CULTURE DEVICE SENSOR CAPS, SYSTEMS, AND METHODS

(71) Applicant: CORNING INCORPORATED, Corning, NY (US)

(72) Inventors: Christopher Bowman Horner, Santa Cruz, CA (US); Amy Claire Kauffman, Kittery, ME (US)

(73) Assignee: CORNING INCORPORATED, Corning, NY (US)

( * ) Notice: Subject to any disclaimer, the term of this patent is extended or adjusted under 35 U.S.C. 154(b) by 515 days.

(21) Appl. No.: 18/284,949

(22) PCT Filed: Mar. 30, 2022

(86) PCT No.: PCT/US2022/022489
§ 371 (c)(1),
(2) Date: Sep. 29, 2023

(87) PCT Pub. No.: WO2022/212462
PCT Pub. Date: Oct. 6, 2022

(65) Prior Publication Data

US 2024/0174968 A1 May 30, 2024

Related U.S. Application Data

(60) Provisional application No. 63/168,639, filed on Mar. 31, 2021.

(51) Int. Cl.

| | |
|---|---|
| *C12M 1/34* | (2006.01) |
| *C12M 1/00* | (2006.01) |
| *C12M 1/24* | (2006.01) |
| *C12M 1/36* | (2006.01) |

(52) U.S. Cl.
CPC ............ *C12M 41/34* (2013.01); *C12M 23/08* (2013.01); *C12M 23/28* (2013.01); *C12M 23/38* (2013.01); *C12M 41/26* (2013.01); *C12M 41/48* (2013.01)

(58) Field of Classification Search
CPC ...... C12M 41/34; C12M 41/26; C12M 41/48; C12M 41/32; C12M 23/08; C12M 23/28; C12M 23/38
See application file for complete search history.

(56) References Cited

U.S. PATENT DOCUMENTS

| | | | | |
|---|---|---|---|---|
| 3,757,979 A * | 9/1973 | Berghahn | B65D 55/02 116/200 |
| 2014/0182362 A1 | 7/2014 | Potyrailo et al. | |

(Continued)

FOREIGN PATENT DOCUMENTS

| | | | |
|---|---|---|---|
| CN | 101886039 B * | 11/2014 | C12M 23/28 |
| EP | 3718632 A1 | 10/2020 | |

(Continued)

OTHER PUBLICATIONS

Machine Translation of CN 101886039 B (Year: 2026).*

(Continued)

*Primary Examiner* — Michael L Hobbs

(57) ABSTRACT

A disposable sensor cap (100) configured to attach to a cell culture device comprises a plurality of sensors for measuring cell culture media conditions. For example, the plurality of sensors (180) may measure dissolved gases and essential molecules of choice without the risk of contamination of the vessel. The sensors may be integrated in a body (150) of the sensor cap. During the measurement period, a small volume of cell culture media may be captured in a sampling chamber of the sensor cap when the cell culture vessel is tipped. An inductor coil (160) on the sensor cap allows for noninvasive wireless reading of the measurements.

27 Claims, 9 Drawing Sheets

(56) References Cited

U.S. PATENT DOCUMENTS

| | | | | |
|---|---|---|---|---|
| 2015/0185173 | A1 | 7/2015 | Potyrailo et al. | |
| 2016/0146748 | A1 | 5/2016 | Reuel et al. | |
| 2016/0184817 | A1* | 6/2016 | Jooris | B01L 3/502715 436/164 |
| 2017/0205356 | A1* | 7/2017 | Assimiti | G01N 21/78 |
| 2020/0264122 | A1 | 8/2020 | Reuel et al. | |
| 2020/0347338 | A1 | 11/2020 | Selzer et al. | |
| 2021/0087508 | A1 | 3/2021 | Cremonese | |

FOREIGN PATENT DOCUMENTS

| | | | | |
|---|---|---|---|---|
| EP | 3718632 | B1 * | 1/2022 | B01L 3/50825 |
| FR | 2955591 | A1 | 7/2011 | |
| JP | 2002-537851 | A | 11/2002 | |
| JP | 2005-531300 | A | 10/2005 | |
| JP | 2016-505850 | A | 2/2016 | |
| JP | 2017-502294 | A | 1/2017 | |
| TW | I658783 | B | 5/2019 | |

OTHER PUBLICATIONS

International Search Report and Written Opinion of the International Searching Authority; PCT/US2022/022489; mailed on Jul. 4, 2022, 11 pages; European Patent Office.

Chinese Patent Application No. 202280027470.X, Office Action dated Apr. 24, 2026, 5 pages (English Translation only), Chinese Patent Office.

* cited by examiner

CELL CULTURE DEVICE SENSOR CAPS, SYSTEMS, AND METHODS

CROSS-REFERENCE TO RELATED APPLICATIONS

This is a national stage application under 35 U.S.C. § 371 of International Application No. PCT/US2022/022489, filed Mar. 30, 2022, which claims the benefit of priority under 35 U.S.C. § 119 of U.S. Provisional Application Ser. No. 63/168,639 filed on Mar. 31, 2021, the content of which are relied upon and incorporated herein by reference in their entirety.

FIELD OF THE INVENTION

This description relates generally to cell culture sensor devices, systems, and methods and more particularly relates to sensor caps for real time analysis and monitoring in cell culture devices.

BACKGROUND

Establishing and maintaining cell and tissue culture practices can be challenging. For users to develop troubleshooting skills for cell culture, a significant amount of training and practice is required to learn proper technique, fundamental aspects of good practice, and to build awareness of a broad range of issues that can arise. However, conventional cell culture monitoring technologies are time consuming and invasive. One of the most challenging aspects of cell and tissue culture practices is the fact that many steps of the cell or tissue culture process are carried out by users and thus are susceptible to human error. For example, human error associated with such "hands-on" experimentation exponentially increases the opportunity for contamination or for other errors to occur, leading to unhealthy cultures, ruined experiments, and other costly outcomes. Therefore, to reduce the opportunity for contamination and other errors during cell culture, measures to reduce or remove human judgement or "hands-on" manipulation are needed.

SUMMARY

In an aspect described herein, a sensor cap for a cell culture device comprises a cylindrical body, a sample collection chamber, and a plurality of sensors. The cylindrical body has a closed end and an open end, wherein the open end is configured to attach to a cell culture device. The sample collection chamber is disposed on an interior surface of the cylindrical body. The plurality of sensors is in communication with the sample collection chamber.

In an embodiment, the cap comprises a plurality of inductor coils disposed on an exterior surface of the cylindrical body. In an embodiment, each inductor coil corresponds to and is in communication with a sensor in the plurality of sensors. In an embodiment, the inductor coils are concentrically disposed on the closed end of the cap.

In an embodiment, the open end comprises threads configured to attach to corresponding threads on a cell culture device.

In an embodiment, the exterior of the cap comprises textured regions.

In an embodiment, the cap is disposable.

In an embodiment, the plurality of sensors is integrated in the body of the sensor cap.

In an embodiment, the plurality of sensors is attached to the body of the sensor cap.

In an embodiment, the plurality of sensors comprises a dissolved gas sensor, an essential molecule sensor, a cell culture condition sensor, or a combination thereof. In an embodiment, the dissolved gas sensor measures dissolved oxygen or carbon dioxide. In an embodiment, the essential molecule sensor measures sugar, lactic acid, ammonium, salts, vitamins, amino acids, or pyruvate content. In an embodiment, the sugar content comprises glucose content. In an embodiment, the cell culture condition sensor measures pH or osmolality. In an embodiment, a sensor for microbial contamination that measures bacterial, fungi, or other micro-contaminates could be included in the plurality of sensors.

In an embodiment, the plurality of sensors comprises inductance-capacitance sensors.

In an embodiment, the cell culture device comprises a cell culture media bottle, a shaker flask, a cell culture flask, a multilayered cell culture flask, multilayer cell culture vessel, cell culture spinner flask, or a cell culture roller bottle.

In an aspect described herein, a cell culture media monitoring system is configured to non-invasively monitor cell culture media. The system comprises a cell culture vessel comprising a cell culture chamber, the cell culture chamber having a surface on which cells are cultured; and a sensor cap configured to attach to the cell culture vessel. The sensor cap comprises a cylindrical body having a closed end and an open end, wherein the open end is configured to attach to a port on the cell culture vessel; a sample collection chamber disposed on an interior surface of the cylindrical body; and a plurality of sensors in communication with the sample collection chamber.

In an embodiment, the system further comprises a controller module configured to control the system.

In an embodiment, the system further comprises a communications module configured to transfer measurement data from the sensor cap to a data processor. In an embodiment, the communications module is configured to communicate through at least one of a wired connection and a wireless connection.

In an embodiment, the system further comprises a data processing device configured to receive transmitted data collected by the sensor cap.

In an aspect described herein, a method of measuring cell culture media conditions comprises attaching a sensor cap to a cell culture device, wherein the cell culture device comprises a cell culture surface for culturing cells and a volume of cell culture media; tilting the cell culture device to flow cell culture media to the sensor cap, wherein a sample of the cell culture media is collected in a sample collection chamber in the sensor cap; and measuring cell culture media conditions of the sample via a plurality of sensors in the sensor cap.

In an embodiment, the sample is collected from an area other than the cell culture surface.

In an embodiment, the plurality of sensors measures dissolved gases, essential molecules, cell culture conditions, or a combination thereof.

In an embodiment, the method further comprises transmitting data collected by the sensor cap during the measurement step to a data processing device.

In an embodiment, the data is transmitted through non-invasive wireless reading of inductor coils on an exterior surface of the sensor cap. In an embodiment, the noninvasive wireless reading is through a microcontroller board. In an embodiment, the noninvasive wireless reading is through a radio frequency identification (RFID) chip.

In an embodiment, the method further comprises monitoring cell culture media conditions in the cell culture device by analyzing the collected data. In an embodiment, the method further comprises providing an output of the measured data collected by the sensor cap.

In an embodiment, the plurality of sensors is small and centralized in the cap, wherein a hydrophobic filter membrane can be affixed on the outer perimeter of the sensors without interference with the inductor coils. Such an embodiment would allow for passive gas exchange and multiple readings to be performed. For example, the cell culture vessel may be disposed or fixed onto a tilting plate that may allow for sample exchange inside of the collection chamber.

In an embodiment, a cell culture vessel comprises a plurality of caps, wherein one or more of the plurality of caps comprises the sensor cap. Such an embodiment would allow for multiple samplings and the support of perfusion vessels without interruption.

DETAILED DESCRIPTION

Figure 1A:
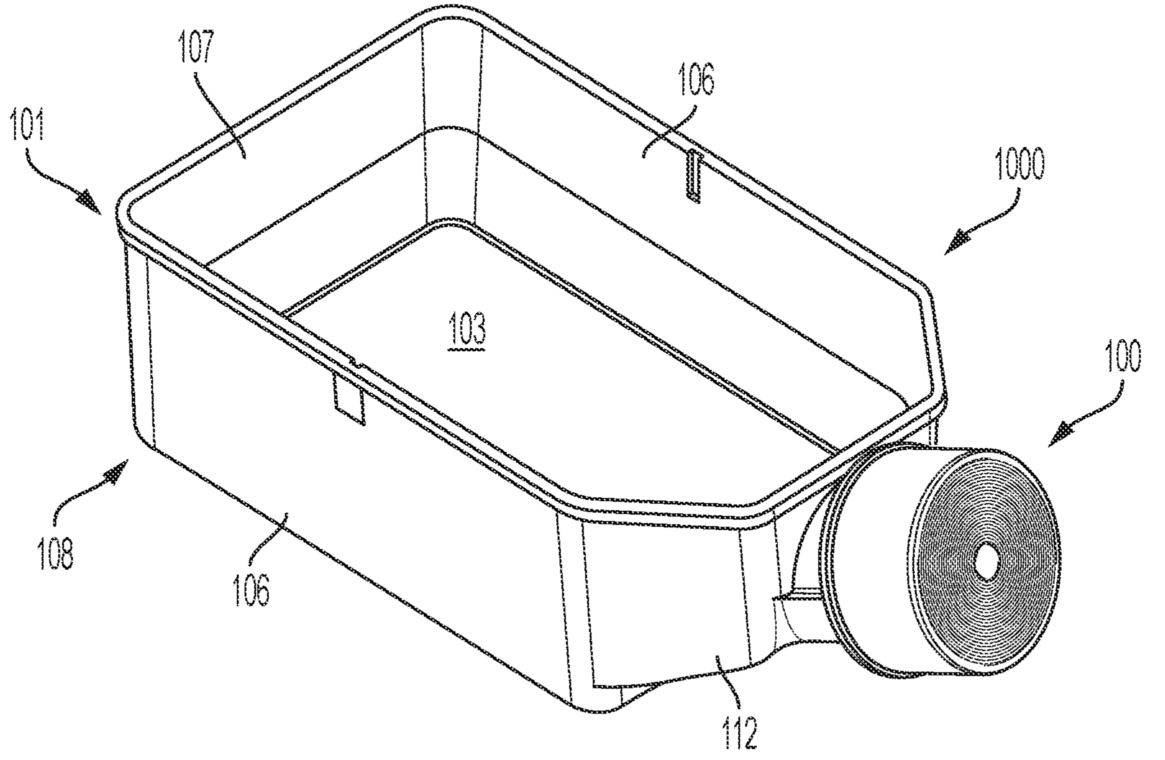
FIG. 1A shows a perspective view of a sensor cap assembled to a cell culture device in accordance with embodiments of the present disclosure.

A critical aspect of cell culture practices includes monitoring dissolved gases and essential molecules in the growth media. The dissolved gases and essential molecules dynamically change while the cells grow and can have both positive and deleterious effects on cells, depending on the concentrations of the dissolved gases and essential molecules as well as the respective needs of the cells. As a nonlimiting example, the concentration of dissolved oxygen can promote hyperoxic (above normal), normoxic (normal), and hypoxic (below normal) levels which can greatly affect both bacterial and mammalian cell culture growth rate and survival. Direct measurement of oxygen content is not universally available, and conventional monitoring practices involve invasive procedures that require removal of a sample of the culture media from the cell culture vessel or the placement of an electrode or probe into the cell culture vessel to read dissolved oxygen. Such practices are time consuming, invasive, require expensive specialized equipment, and greatly increase the opportunity for contamination of the vessel.

In an aspect, a sensor cap according to embodiments described herein is embedded with electronic sensors to monitor levels of macromolecules, gases, or other compounds in cell culture media in real-time. The sensor cap may wirelessly transmit the data to a mobile device.

In contrast to conventional technologies, when using a sensor cap according to embodiments described herein, the vessel can be tilted to capture a small liquid sample, complete the analysis, and wirelessly transfer the results to a mobile device (such as a computer or tablet) with no exposure to outside contaminants. The cap can then be disposed of and replaced with typical vented or unvented cap to continue cell growth appropriately without the risk of contamination.

In an aspect, a sensor cap for a cell culture flask comprises an integrated sensor that measures dissolved gases and molecules in cell culture media in real-time. The sensor cap can measure molecules in cell culture media non-invasively and transmit the output data wirelessly. Conventional practices for measuring dissolved molecules require invasive procedures to remove a sample of the media from the culture vessel and perform the assay outside of the vessel or place the sensor or electrode directly into the media where the cells are present. Conventional methods also increase the risk for vessel contamination and, if the assay is performed outside of the vessel, may not achieve accurate results.

Sensor caps according to embodiments described herein are compatible with cell culture devices. For example, sensor caps may be used with any device or vessel that has an aperture or port, such as a threaded port for attaching a lid or cap, wherein the device or vessel is suitable for conducting cell culture experiments. In some embodiments, sensor caps are interchangeable with existing or conventional caps for commercially available cell culture devices and vessels, such as the threaded orange caps provided with Corning® cell culture devices (Corning Incorporated, Corning, NY).

In some embodiments, sensor caps are compatible with cell culture devices or vessels. In some embodiments, the cell culture device or vessel supports two-dimensional (2D) cell culture, such as culturing adherent cells (e.g., in a monolayer). In some embodiments, the cell culture device or vessel supports three-dimensional (3D) cell culture, such as culturing non-adherent cells (e.g., by suspension). In some embodiments, the cell culture device or vessel support both 2D and 3D cell culture. In some embodiments, sensor caps are compatible with cell culture devices such as cell culture or tissue culture flasks. In some embodiments, the cell culture device comprises a cell culture media bottle, a shaker flask, a cell culture flask, a multilayered cell culture flask, multilayer cell culture vessel, cell culture spinner flask, or a cell culture roller bottle. Nonlimiting examples of cell culture media bottles include Corning® Easy Grip Polypropylene, PET, or Polycarbonate Storage Bottle (Corning Incorporated, Corning, NY), Corning® PYREX® Glass Storage Bottle (Corning Incorporated, Corning, NY), SCIENCEWAR® Storage Bottle (Bel-Art Products-SP Scienceware, South Wayne, NJ), and Nalgene® Storage Bottle (Thermo Fisher Scientific, Waltham, MA). Nonlimiting examples of shaker flasks include Corning® Erlenmeyer Shake Flask (Corning Incorporated, Corning, NY) and Greiner Bio-One Erlenmeyer Shaker Flask (Greiner BioOne North America, Inc., Monroe, NC). Nonlimiting examples cell culture flask include Corning® Falcon® Cell Culture Flasks (Corning Incorporated, Corning, NY), Nunc® EasY-Flasks (Thermo Fisher Scientific, Waltham, MA). Nonlimiting examples of multilayered cell culture flasks include Corning® HYPERFlask (Corning Incorporated, Corning, NY), Falcon® Multi-Flask (Corning Incorporated, Corning, NY), MilliCell® HY Multilayer Culture Flask (Merck KGaA in Darmstadt, Germany), Nonlimiting examples of multilayer cell culture vessels include Corning® CELL-STACK® (Corning Incorporated, Corning, NY) and Corning® HYPERStack (Corning Incorporated, Corning, NY). Nonlimiting examples of cell culture spinner flasks include Corning® Disposable Plastic Spinner Flask (Corning Incorporated, Corning, NY), Celstir® Suspension Culture Flask (DWK Life Sciences GmbH, Wertheim, Germany), Corning® Reusable Glass Spinner Flask (Corning Incorporated, Corning, NY), and ProCulture® Complete Spinner Flask (Corning Incorporated, Corning, NY). Nonlimiting examples of cell culture roller bottles include Corning® Polystyrene Roller Bottle (Corning Incorporated, Corning, NY), Corning® Expanded Surface Polystyrene Roller Bottle (Corning Incorporated, Corning, NY), PYREX® Roller Bottle with Screw Cap (Corning Incorporated, Corning, NY), VWR Roller Bottle (VWR International, LLC, Radnor, PA), Nunc® In Vitro Roller Bottle (Thermo Fisher Scientific, Waltham, MA), and CELLMASTER™ Cell Culture Roller Bottle (Greiner BioOne North America, Inc., Monroe, NC).

In an aspect, sensor caps according to embodiments described herein provide a user-friendly device. Users may need minimal training to use the sensor caps. For example, training may include reading an instruction sheet commercially provided with a sensor cap.

Furthermore, the sensor caps described herein limit the risk of cell culture vessel contamination by decreasing "hands-on" steps by the user during experimentation and cell culture. The sensor cap allows for non-invasive testing of the cell culture conditions. For example, the sensor cap may collect a small sample from free-flowing media in the cell culture device while the cell culture device remains closed. In some embodiments, the sensor cap comprises a collection area for the sample fluid. In some embodiments, the sample fluid tested remains in the collection area and is not released back to the free-flowing media in the cell culture device. In some embodiments, the sensor cap allows tested sample fluid to be re-entered into the free-flowing media within the cell culture device. In embodiments, sample fluid is collected and tested from an area where cells are not growing—for example, sample fluid is not collected from a cell culture surface, such as cell culture surface located on an interior bottom surface of a cell culture device.

In an aspect, sensor caps according to embodiments herein may be disposable. A sensor cap according to embodiments described herein may be used for a predetermined amount of time and then may be disposed. A new sensor cap may be used for each new cell culture experiment. In some embodiments, sensor caps as described herein provide longer-term testing, such as testing over multiple hours or over multiple days. In some embodiments, the sensor cap may be used for the duration of a cell culture experiment. In some embodiments, the cell culture experiment may extend for any suitable amount of time to conduct the experiment. As a nonlimiting example, the cell culture experiment may last hours or weeks, for example from about 72 hours to about 3 weeks. Sensor caps according to embodiments described herein are disposed after the cell culture experiment is finished, such as at the time of disposing the used cell culture container, device, or vessel.

In some embodiments, the cap may be fitted with a hydrophobic filter ring that allows for passive gas exchange into the cell culture vessel. Such embodiments may extend the cell culture experiment to the discretion of the experimenter and may extend the given cell line for up to months of culture.

Features will now be described more fully hereinafter with reference to the accompanying drawings in which exemplary embodiments of the disclosure are shown. Whenever possible, the same reference numerals are used throughout the drawings to refer to the same or like parts. However, this disclosure can be embodied in many different forms and should not be construed as limited to the embodiments set forth herein.

Figure 1B:
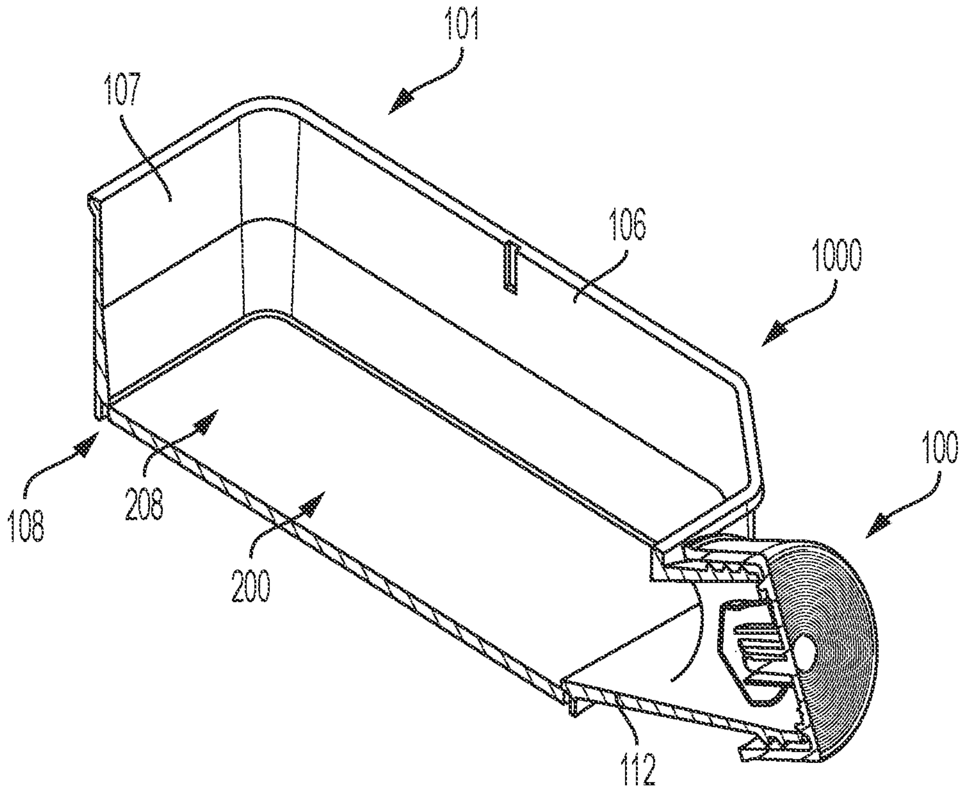
FIG. 1B shows a cross-sectional perspective view of a sensor cap assembled to a cell culture device in accordance with embodiments of the present disclosure.
Figure 1C:
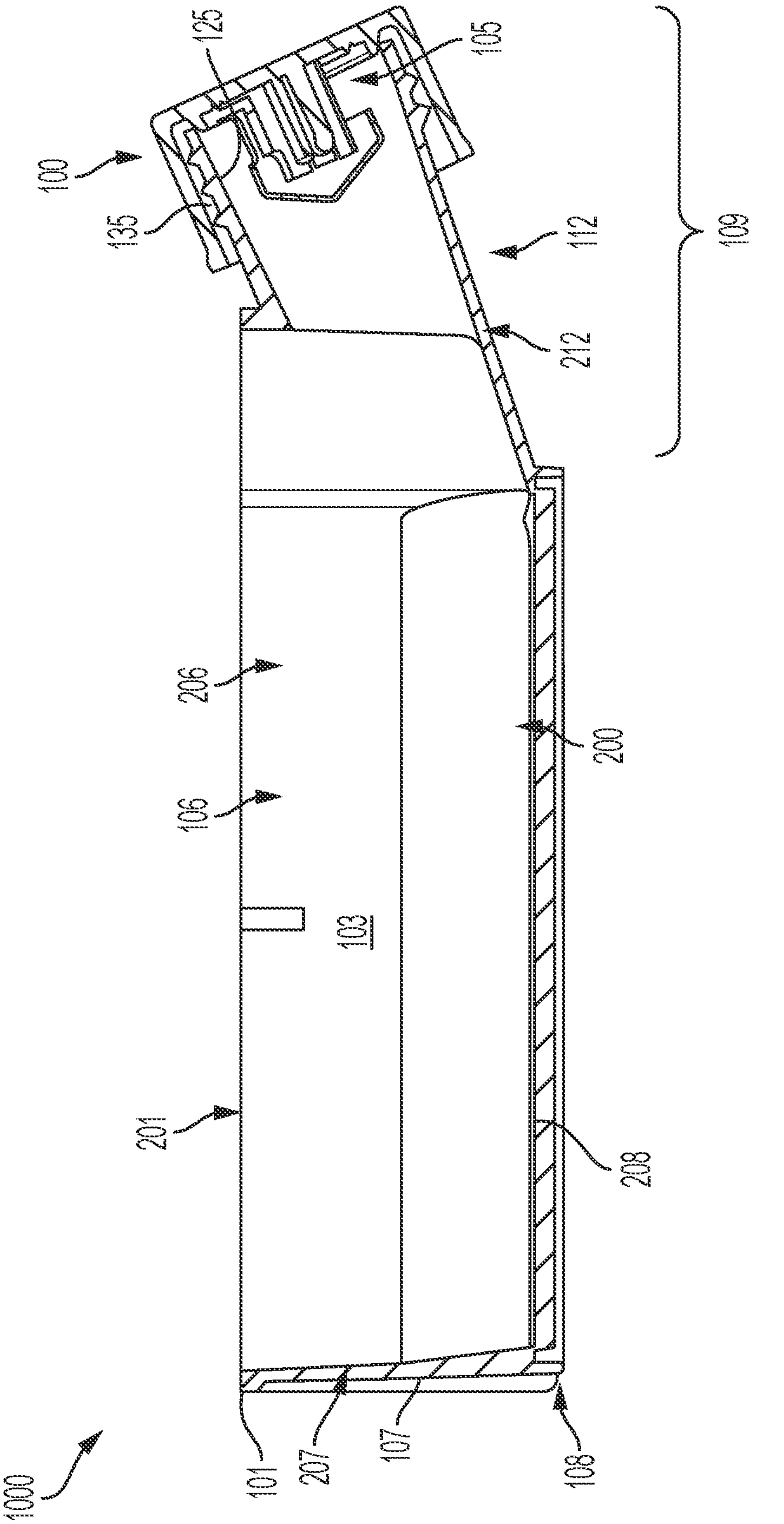
FIG. 1C shows a cross-sectional side view of a sensor cap assembled to a cell culture assembly in accordance with embodiments of the present disclosure.

FIG. 1A shows a perspective view of a sensor cap assembled on a cell culture device. As shown in FIG. 1A, the cell culture device may comprise a Corning® T75 tissue culture flask (available from Corning Incorporated, Corning, NY). FIG. 1B shows a cross-sectional perspective view of the assembly. FIG. 1C shows a cross-sectional side view of the sensor cap and flask assembly, which shows that the sensor cap does not contact the cell culture surface during cell culture applications. In embodiments, the sensor cap is positioned a distance away from the cell culture media so that the sensor cap contacts cell culture media only when a sample is collected by tilting the cell culture vessel towards the sensor cap.

As shown in FIGS. 1A-C, a sensor cap 100 is attached to a cell culture vessel 1000. A cell culture vessel (e.g., flask) can provide a sterile chamber for culturing cells. In embodiments, the cell culture vessel 1000 can include a bottom 108, a top 101, and endwall 107 and sidewalls 106, each having internal surfaces that contact liquid media and cells in culture. These internal surfaces define the cell culture chamber 103.

In some embodiments, at least one of the internal or interior surfaces can be more particularly adapted for cell growth. For example, a cell culture surface may be treated with a coating to encourage or discourage cells to stick to a surface. In some embodiments, the cell culture vessel comprises a cell adherent coating on one or more interior surfaces. Any suitable cell adherent coating may be used, such as the nonlimiting examples of Corning® CellBIND® (Corning Incorporated, Corning, NY), Corning® Primaria™ (Corning Incorporated, Corning, NY), and Corning® PureCoat™ amine and carboxyl (Corning Incorporated, Corning, NY) surfaces. In some embodiments, the cell culture vessel comprises a cell non-adherent coating on one or more interior surfaces. Any suitable cell non-adherent coating may be used as the coating, such as a Corning® Ultra-Low Attachment (Corning Incorporated, Corning, NY) surface. Nonlimiting examples of ultra-low binding materials for coating include one or more of perfluorinated polymers, olefins, agarose, non-ionic hydrogels such as polyacrylamides, polyethers such as polyethyleneoxide, polyols such as polyvinylalcohol or mixtures thereof.

The cell culture vessel 1000 has a port or aperture 105 configured to attach to a cap, such as sensor cap 100, and a neck 112 connecting the port or aperture 105 to the cell culture chamber 103. In embodiments the aperture can be releasably sealed. For example, in embodiments, the aperture 105 section of the neck 112 can have threads 125 (either interior or exterior) that allow a cap 100 to be releasably sealed by the cap 100 having a complimentary threaded structure 135. The aperture 105 combined with the neck 112 is the necked opening 109. The necked opening 109 extends through a wall of the cell culture chamber 103 and is in fluid communication with the cell culture chamber 103. The necked opening 109 allows liquid to be introduced and removed from the cell culture chamber 103 (the interior) of the vessel 1000.

The cell culture surface 200 of the vessel 1000 is, in embodiments, the interior surface 208 of the bottom 108 of the vessel 1000 when the vessel 1000 is oriented for cell growth. In embodiments, the vessel 1000 is oriented for cell growth when the vessel 1000 is placed with the bottom 108 of the vessel 1000 flat on a surface. The vessel 1000 may also have sidewalls 106 and an endwall 107 opposite the necked opening 109, a top 101 and bottom 108. In embodiments the top 101 is opposite the cell culture surface 200 of the vessel 1000. In embodiments, the necked opening 109 is opposite the endwall 107 of the vessel 1000. Each of these structures (the necked opening 109, the top 101, the bottom 108, the sidewalls 106 and the endwall 107) of the vessel 1000 have internal surfaces facing inside the vessel 1000. That is, the top 101 has an interior surface 201. The end wall 107 has an interior surface 207. The sidewalls 106 have interior surfaces 206. The neck 112 has an internal surface 212. The inside of the vessel is the cell culture chamber 103, the space inside the vessel 1000, defined by the top 101, the bottom 108, the sidewalls 106 and the endwall 107 where cells reside inside the vessel 1000. For example, in some embodiments, the cell culture chamber 103 includes an internal spatial volume of the vessel.

Cell culture devices according to embodiments described herein may be formed of any suitable material. In some embodiments, cell cultures devices are formed of a polymeric material. Nonlimiting examples of polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers.

Sensor caps as described in embodiments herein may be formed of any suitable material. For example, sensor caps may be fabricated via additive manufacturing, such as 3D printing, or molding techniques, such as rotational, injection, blow, compression, extrusion, or thermoforming molding techniques. In some embodiments, sensor caps may by formed of a low-cost, biocompatible material. For example, sensor caps may be formed of a polymeric material. Nonlimiting examples of polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. In some embodiments, the sensor caps are formed of polypropylene.

Sensor caps according to embodiments described herein are configured to be releasably attached to a cell culture vessel. For example, the sensor cap may be attached to an aperture or port of a cell culture vessel to form a liquid-tight seal on a cell culture vessel. The sensor cap may comprise threading or other connecting means for attachment to the cell culture device. For example, the sensor cap may be rotated to engage the threaded portion on an interior surface of the cap to corresponding threading on the external surface of a port or aperture region of the cell culture device. In some embodiments, sensor caps may be configured to snap on to the port or aperture of the cell culture device. In some embodiments, sensor caps may have a Quick-Connect configuration to attach to a port or aperture of a cell culture device.

Figure 2:
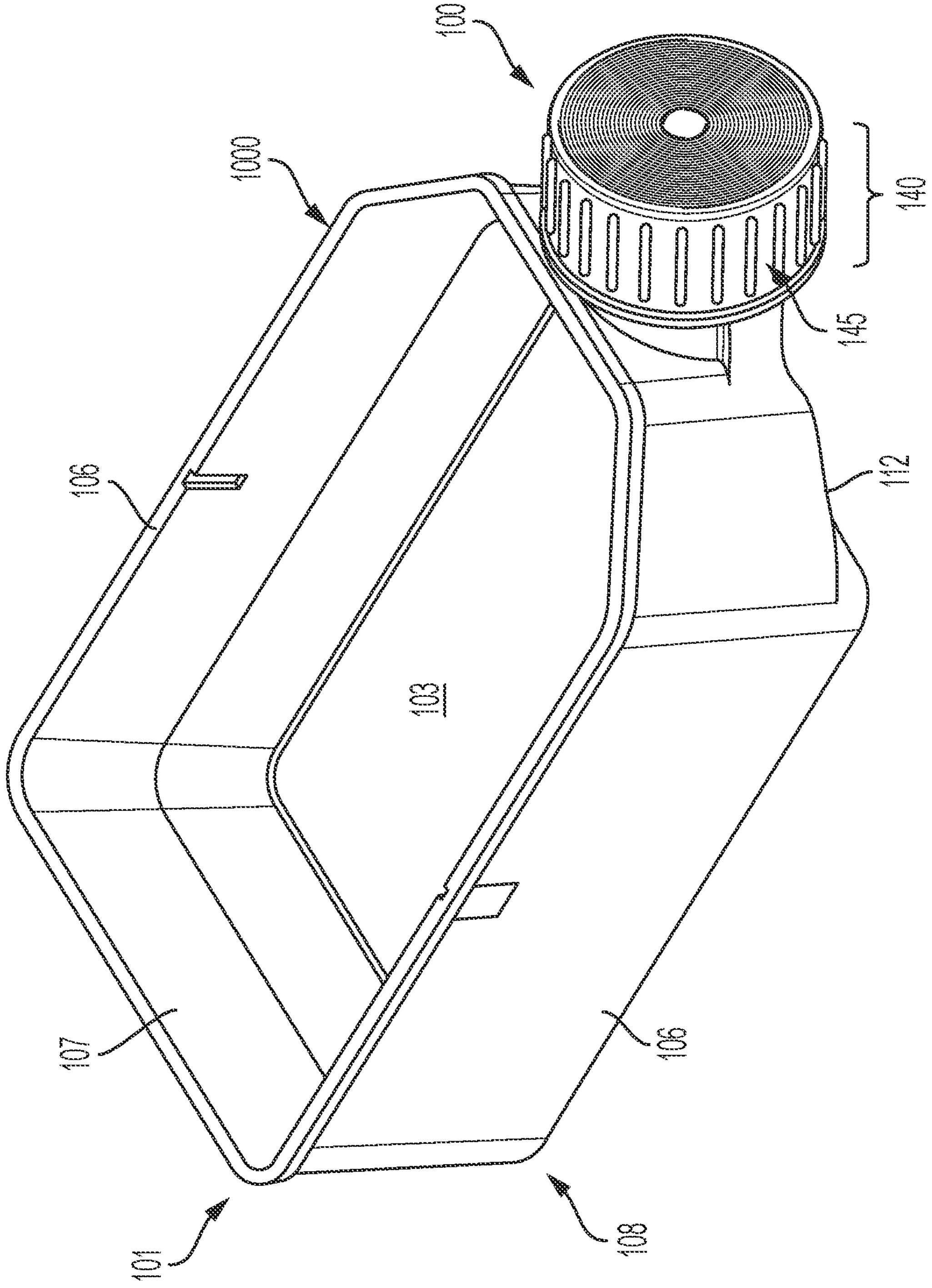
FIG. 2 shows a perspective view of a sensor cap assembled to a cell culture device in accordance with embodiments of the present disclosure.

In some embodiments, the exterior of the cap may comprise textured regions. For example, the cap may comprise ridges or other textured features that help the user to grip the cap. FIG. 2 shows an embodiment of a sensor cap 100 attached to a cell culture vessel 1000. The sensor cap 100 comprises a textured region 140. As shown in FIG. 2, the textured region 140 comprises a plurality of ridges 145.

Sensor caps according to embodiments described herein may comprise a plurality of sensors. In some embodiments, the plurality of sensors may be integrated in the sensor cap. For example, sensors may be formed as an integrated part of the sensor cap during a 3D printing process of the sensor cap. In some embodiments, the plurality of sensors may be attached to a sensor cap. For example, the plurality of sensors may be attached by any suitable attachment means, such as by laser, ultrasonic welding, thermal bonding, other heat sealing, adhesives, or a combination thereof.

Sensor caps according to embodiments described herein may be formed by any suitable means. In some embodiments, sensor caps may be formed by thermoforming or molding techniques. In some embodiments, sensor caps may be formed by three-dimensional additive printing (3D printing).

In some embodiments, a plurality of sensors may be integrally formed in the sensor cap using 3D printing. A sensor cap structure may be formed by 3D printer equipment using a 3D printing technique. For example, liquid metal paste may be used in 3D printing equipment to produce microelectronic components of the sensors, such as resistors, capacitors, and inductors. Resistors may comprise conductive wires in the sensor cap. In some embodiments, resistors may comprise a meander shape. In some embodiments, resistance of each wire may be determined by the wire length, cross-sectional area, and/or the resistivity of the material of the wire. Inductors may comprise any suitable shape. In some embodiments, inductors may comprise a shape of a spiral coil. In some embodiments, inductance may be determined by the number of turns of the coils and/or the enclosed area of the coils. Capacitors may be constructed in the form of two parallel-plates. In some embodiments, capacitance may be determined by the distance between the two plates and/or the area of the plates.

A structural body of the sensor cap may be formed by 3D printing, with cavities designed in the body of the 3D structure. The cavities may be filled with liquid metal paste to form conductive electrical structures. For example, injection holes may be used as inlet and outlet ports for solenoid channels when filling the cavities with liquid metal paste. Cavities may also be formed on an exterior surface of the sensor cap to form contact pads. For example, the contact pads may comprise radio frequency (RF) reader contact pads or ground-signal-ground pads.

In some embodiments, the sensor cap comprises an inductor-capacitor circuit, such as an LC-resonant circuit. In an embodiment, the sensor cap may comprise an LC-resonant circuit. The LC-resonant circuit may be formed from a capacitor (sensor probe) disposed on an interior surface of the sensor cap and an inductor disposed on an exterior surface of the sensor cap. In some embodiments, the inductor may comprise a spiral shape. The sensor cap further comprises a capacitor gap formed by the sample collection chamber. When the cell culture device is tilted toward the sensor cap, liquid media in the device travels to the sensor cap. A sample of the liquid media is trapped in the sample collection chamber, and the collected media sample acts as the dielectric material in the capacitor gap.

The circuit may be wirelessly readable. For example, in some embodiments, the sensor cap may comprise a 3D radio-frequency circuit for passive wireless sensing. The value of resonance frequency of the collected sample may be detected wirelessly using a radio frequency (RF) reader. As the cell culture experiment progresses, the dielectric constant of the liquid cell culture media changes. The shift in the resonance frequency of the sample collection chamber where sample cell culture media is collected can be detected wirelessly by an inductively coupled reader in real time.

The LC-resonant circuit formed by the plurality of sensors in the sensor cap may detect the conditions of the liquid cell culture media in the cell culture device. The sensing principle is based on the capacitance changes of a sample of the liquid cell culture media due to change or deterioration over time (i.e., during the cell culture experiment). Resonance frequency shifts may be measured via an inductive reader to allow for passive, wireless sensing of the cell culture media without needing to invasively insert sensor probes into a cell culture device and risk disturbing the cell culture surface. In some embodiments, the sensor cap may comprise passive operation, or operation without power consumption. However, sensor caps with active operation are also contemplated. In some embodiments, the sensor cap may comprise wireless reading capability. In some embodiments, the sensor cap may comprise wired reading capability.

Figure 3A:
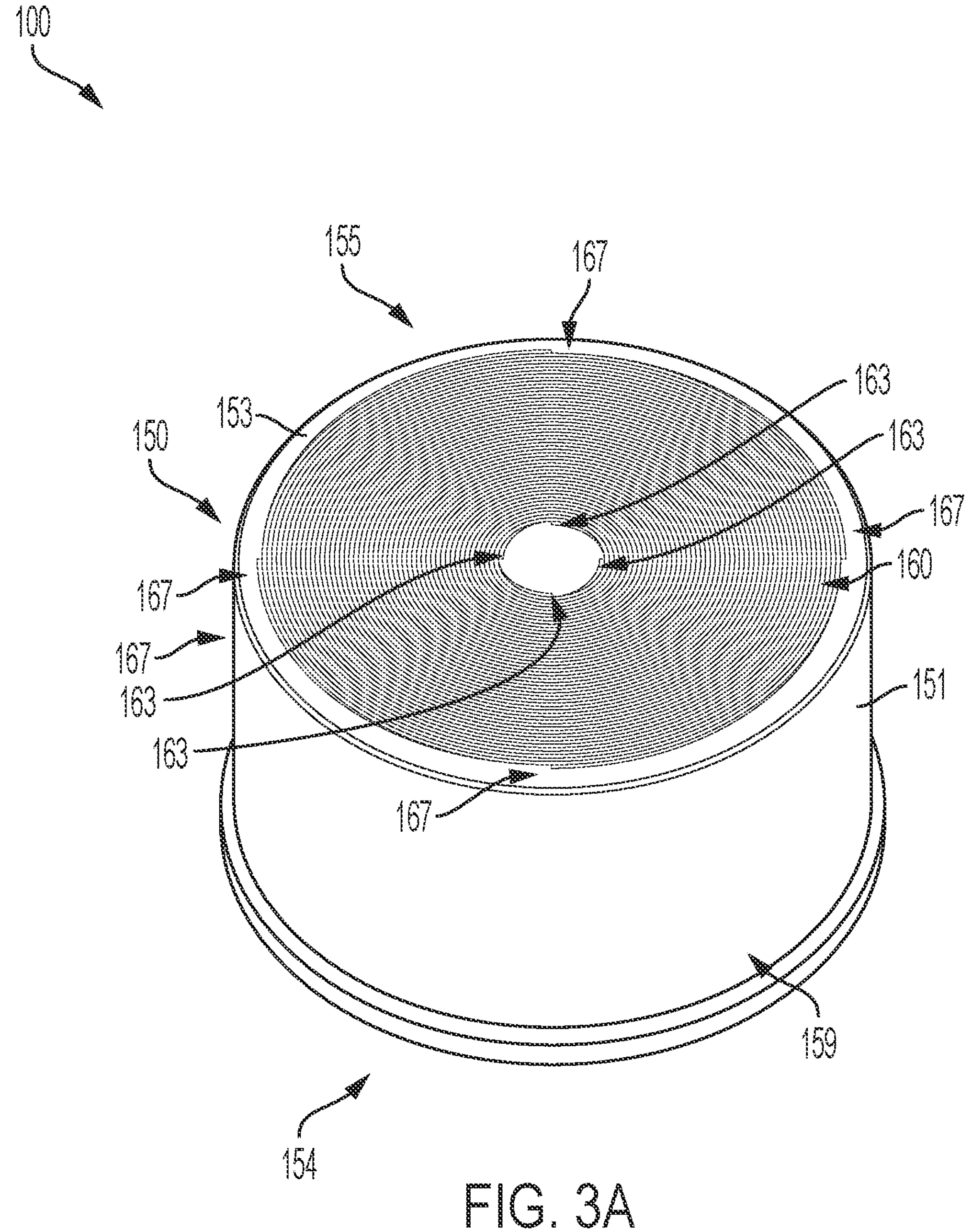
FIG. 3A shows a perspective view of a sensor cap in accordance with embodiments of the present disclosure.
Figure 3B:
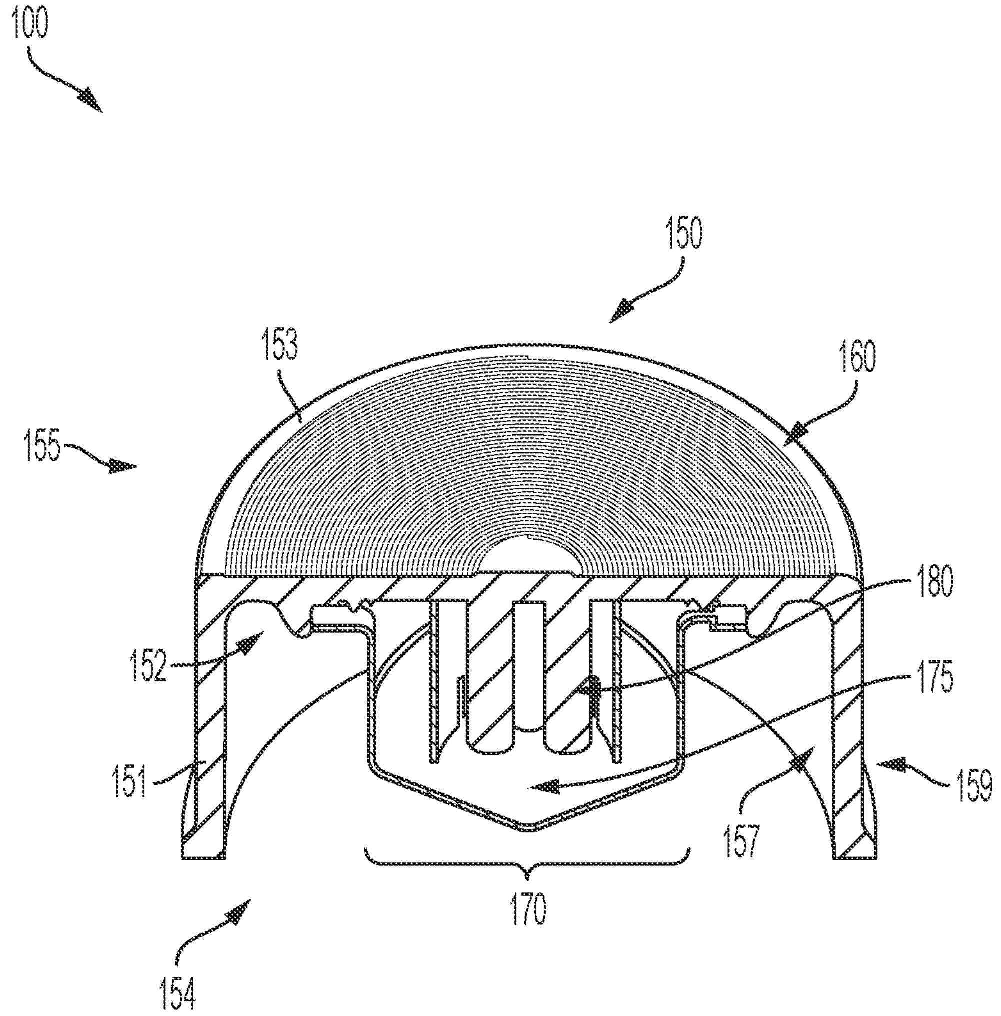
FIG. 3B shows a cross-sectional perspective view of sensor cap components in accordance with embodiments of the present disclosure.

FIG. 3A shows a perspective view of a sensor cap 100 according to embodiments described herein. FIG. 3B shows a cross-sectional perspective view of active components disposed within a sensor cap. The sensor cap 100 comprises a cylindrical body 150. The cylindrical body 150 comprises a sidewall 151, with a closed end 155 disposed on one end of the sidewall 151 and an open end 154 disposed on an opposite end of the sidewall 151. The open end 154 is configured to attach to an opening or aperture of a cell culture device. The sidewall 151 has an interior surface 157 and an exterior surface 159. The closed end 155 has an exterior surface 153 and an interior surface 152.

A plurality of inductor coils 160 may be disposed on the exterior surface 153 of the closed end 155. Each inductor coil may correspond to and be in communication with a sensor in the plurality of sensors disposed on an interior of the sensor cap. Four independent concentric spiral inductor coils 160 are shown in FIG. 3A as a passive method for reading the data from the sensor cap 100. Locations of connections to positive electrode probes 183 within the cap are designated by reference sign 163. Locations of connections corresponding negative electrodes 187 connected to the sample collection chamber are designated by reference sign 167.

A sample collection chamber 175 is disposed on an interior surface 152 of a closed end 155 of the cylindrical body 150. A body of the sample collection chamber component 170 extends from the interior surface 152 of the closed end 155. A plurality of sensors 180 may be integrally disposed in the body 170 or may be attached to the body 180. At an end of the body 170 opposite the closed end 155, the body comprises a sample collection chamber 175. At least a portion of the sample collection chamber 175 is in communication with the cell culture chamber 103. The sample collection chamber 175 defines an interior volume 176 configured to contain a liquid sample 190 of cell culture media, wherein the sample 190 of cell culture media enters the collection chamber 175 and is contained in the collection chamber 175 when the cell culture device 1000 is tilted towards the sensor cap 100. The plurality of sensors 180 is in communication with the sample collection chamber 175.

Figure 4:
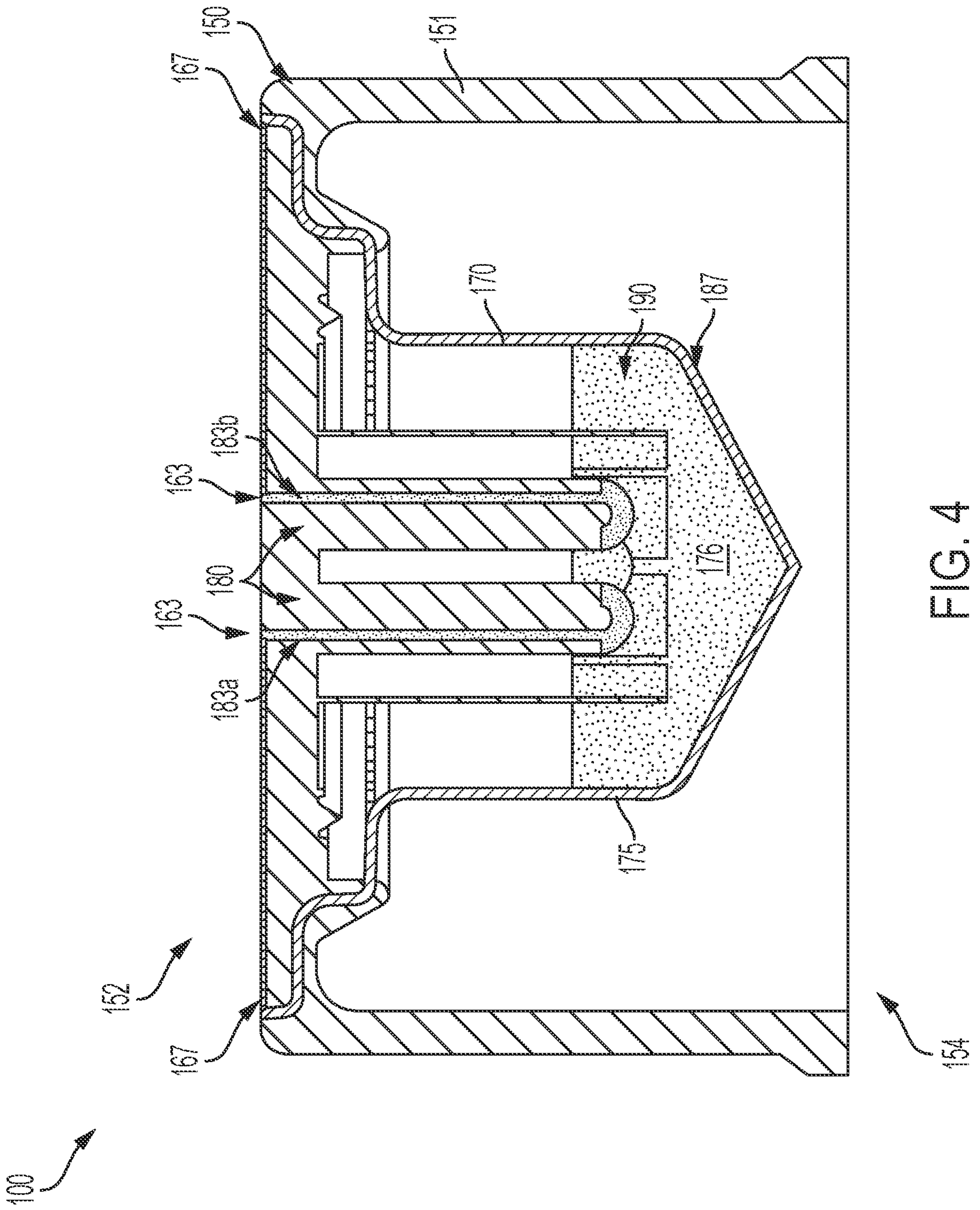
FIG. 4 shows a cross-sectional side view of a sensor cap in accordance with embodiments of the present disclosure.

FIG. 4 shows a cross-sectional side view of the sensor cap 100 showing a plurality of sensors 180. The plurality of sensors 180 comprises positive (+) electrodes 183 used for measuring capacitance of analytes in cell culture media. For example, a first sensor measures a first analyte and includes positive (+) electrode 183*a*, and a second sensor measures a second analyte and includes positive (+) electrode 183*b*. The positive electrodes 183 are connected to inner nodes 163 of the inductance coil 160. A common negative (−) electrode 187 is contained within the sample cup 175 connected to outer node 167 of concentric inductance coils 160. In some embodiments, different analytes may be measured. In some embodiments, each electrode measures a certain analyte. In some embodiments, the sensor cap comprises up to four independent analytes to be measured simultaneously.

The positive electrode (cathode) is typically referred to as the measuring or working electrode, whereas the negative electrode (anode) is the common or reference electrode. The measuring (+) electrode is sensitive to specific ions (for example, the hydrogen ion when measuring pH), wherein the measuring electrode develops a potential (voltage) related to a specific concentration of ion in the solution. The reference (−) electrode provides a stable potential, wherein the measuring electrode is compared against resulting a differential voltage, and therefore a specific pH measurement. Ion-selective electrodes (ISEs) are capable of measuring ions found in biological fluids (such as nonlimiting examples of hydrogen, potassium, calcium, and ammonium, among others) based on potentiometry. Dissolved oxygen measurements may also conduct measurements using the cathode and anode but may use the Clark electrode based on voltammetry (aka amperometry) where the current is measured at a constant voltage due to the presence of reduction/oxidation of the analyte.

Figure 5:
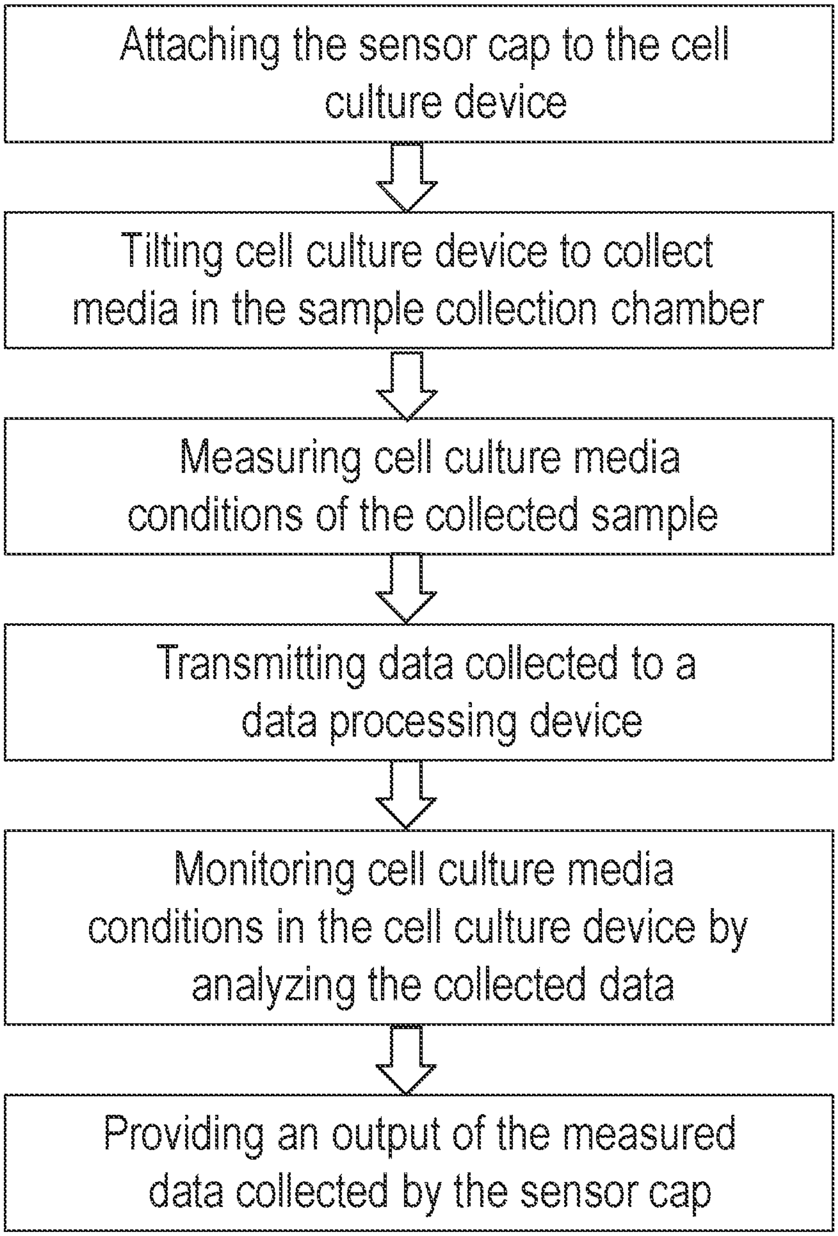
FIG. 5 shows a flowchart of a method according to one or more embodiments described herein.

FIG. 5 shows a flowchart of a method of using a sensor cap according to embodiments described herein. According to embodiments, methods of using the sensor cap comprise attaching a sensor cap to a cell culture device. In some embodiments, the method comprises filling the cell culture device with cells to be cultured, cell culture media, and any additives or supplements for the cell culture experiment. Methods further comprise tilting the cell culture device after a period of time. The cell culture device may be titled after any suitable period of time so as to monitor analyte conditions during the cell culture experiment. The cell culture device may be tilted by any suitable means that allows culture media to be collected in the sample collection chamber of the sensor cap. As a nonlimiting example, a user may physically tilt the cell culture device. As a nonlimiting example, a mechanical device may be used to tilt the cell culture device, such as by mechanical movement triggered by a stage or tilt device that is programmable, such as a tilt platform available for side shaker plates or by adapting other equipment. The cell culture device may be tilted for any amount of time suitable to collect cell culture media in the collection chamber of the sensor cap. For example, the cell culture device may be tilted for about 5 seconds to about 30 seconds or any other amount of time that allows for media to be collected in the collection chamber without disturbing the cell culture surface. The method further comprises measuring the cell culture media conditions of the cell culture device by taking one or more measurements of the media in the collection chamber using the plurality of sensors in the sensor cap. The method further comprises transmitting the data collected from the plurality of sensors to a data processor for analysis.

A disposable sensor cap as described in embodiments herein is configured to attach to a cell culture device, such as a cell culture flask, comprises one or more sensors that can measure dissolved gases and essential molecules of choice without the risk of contamination of the vessel. The sensors may be integrated in a body of the sensor cap. The sensor cap affixes onto the top of the flask with a secure screw action and has no contact with the area in which the cells are grown. The design allows for a small volume of fluid to be captured in the sampling chamber when the vessel is tipped and the cell culture media is trapped during the measurement period. The sensor relies on inductance-capacitance (LC) circuitry where the captured media gets trapped in between the gap of the sensor (upper electrode) and the sampling chamber (bottom electrode) acting as a dielectric material where the resonant frequency (fres) will shift as the liquid changes capacitance values through consumption during cell culture. The cap is designed with an inductor coil located on the upper surface of the cap which enables noninvasive wireless reading of the analyte(s) via a microcontroller board (such as an Arduino BT), a radio frequency identification (RFID) chip, or other wireless transmission capacity. After the data is read and transfer has been completed to user satisfaction, the cap can remain in place and be ready for additional sampling at later times or removed and replaced with a sterile vented cap for continued growth.

In an aspect, sensor caps as described in embodiments herein may test cell culture conditions within a cell culture device. In some embodiments, sensor caps may detect various dissolved gases and molecules. Nonlimiting examples of dissolved gases and molecules for detection by sensor caps include dissolved gases such as oxygen and carbon dioxide. In some embodiments, sensor caps may detect dissolved molecules, metabolites, and nutrients. Nonlimiting examples of dissolved molecules, metabolites, and nutrients that may be tested or assayed include sugars (glucose), lactic acid, ammonium, salts, vitamins, amino acids, and pyruvate. In some embodiments, sensor caps may test or measure cell culture conditions such as pH, osmolality, and other cell culture media characteristics. In an embodiment, a sensor for microbial contamination that measures bacterial, fungi, or other micro-contaminates may be included in a plurality of sensors of a sensor cap as described herein.

A sensor cap according to embodiments described herein is configured to attach to a cell culture device and to collect analyte data within the cell culture device. The sensor cap comprises a body wherein one or more sensors are disposed in the body of the sensor cap. The data for the sensor cap be stored and accessed by any suitable means. In some embodiments, the data collected from sensor readings may be transmitted by a wireless connection to a data processing device. In some embodiments, the data may be transmitted by a wired connection. The collected data may be received by a data receiving device, such as mobile computer or mobile phone. As a nonlimiting example, the sensor cap may comprise an RFID tag and the data for the sensor cap may be accessed via RFID reader. The data may be analyzed on a mobile device equipped with Bluetooth or other data transmission technology or methodology, such as a computer, tablet, or smart phone.

Figure 6:
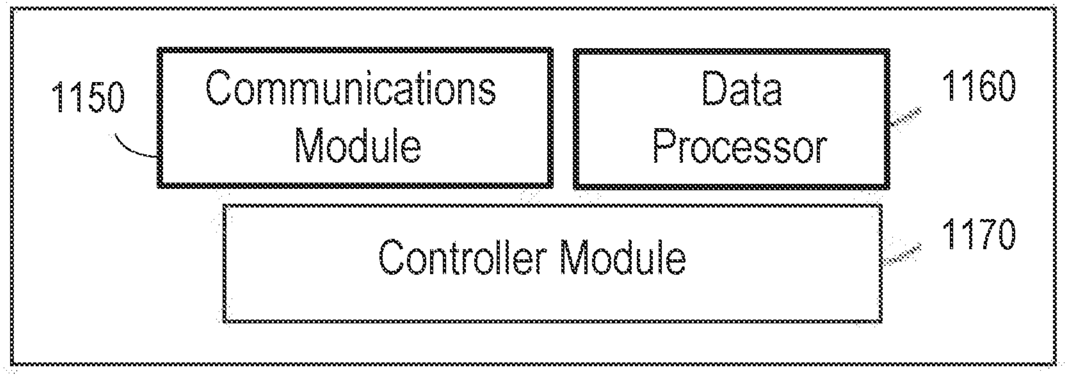
FIG. 6 schematically illustrates components of a sensor cap monitoring system for cell culture monitoring in accordance with embodiments of the present disclosure.

FIG. 6 further illustrates additional components of the sensor cap monitoring system. These components may be incorporated into the sensor cap. As shown, the sensor cap monitoring system may further include a controller module 1170 configured to control the various components of the system. For example, the controller module 1170 may be configured to control one or more sensors in the sensor cap. For example, the controller module 1170 may be configured to distinguish between and control individual sensors in the cap and to distinguish sensor readings. The controller module 1170 may also be configured to control one or both of the communications module 1150 and the data processor 1160. In some embodiments, the controller 1170 may be configured to control frequency of monitoring.

In some embodiments, the sensor cap monitoring system may further include a communications module 1150 configured to transfer data from the sensor cap 100 to a data processor 1160. The communication module 1150 may be configured to communicate through a wired or wireless connection, including, but not limited to, a data connection conforming to one or more of the IEEE 802.11 family of standards (e.g., WiFi), a Bluetooth connection, a cellular network connection, an RF connection, a Universal Serial Bus (USB), an Ethernet connection, or any other data connection. The data processor 1160 may be configured to record and analyze cell culture data received from the sensor cap 100. The communications module 1150, and data processor 1160 may be on a single electronic device or multiple electronic devices, such as one or more desktop computers, laptop computers, tablet PCs, or other computer systems. The controller module 1170, communications module 1150, and data processor 1160 may interact so as to provide certain features to the sensor cap 100. For example, the sensor cap 100 may be adapted to record the cell culture data (e.g., monitoring and testing data for analytes, dissolved gases, pH, or other cell culture conditions) in a non-transitory computer readable medium. In some embodiments, the sensor cap monitoring system may be adapted to allow a user to record and/or analyze cell culture data. In other embodiments, the sensor cap 100 may allow a user to set a monitoring period and/or monitoring frequency, such that cell culture data is recorded and/or analyzed once in a predefined time period for a predefined duration of time. In other embodiments, cell culture data may be recorded and/or analyzed at a defined frequency continuously for an indefinite duration. In other embodiments, the sensor cap 100 may communicate with a remote user device. The remote user device may be, e.g., a mobile phone device, a tablet computer, a desktop computer, a laptop computer or other computing system. The sensor cap 100 may send cell culture data to the remote user device. In some embodiments, the remote user device may be adapted to control the sensor cap 100, including any of the functionality discussed above.

Figure 7:
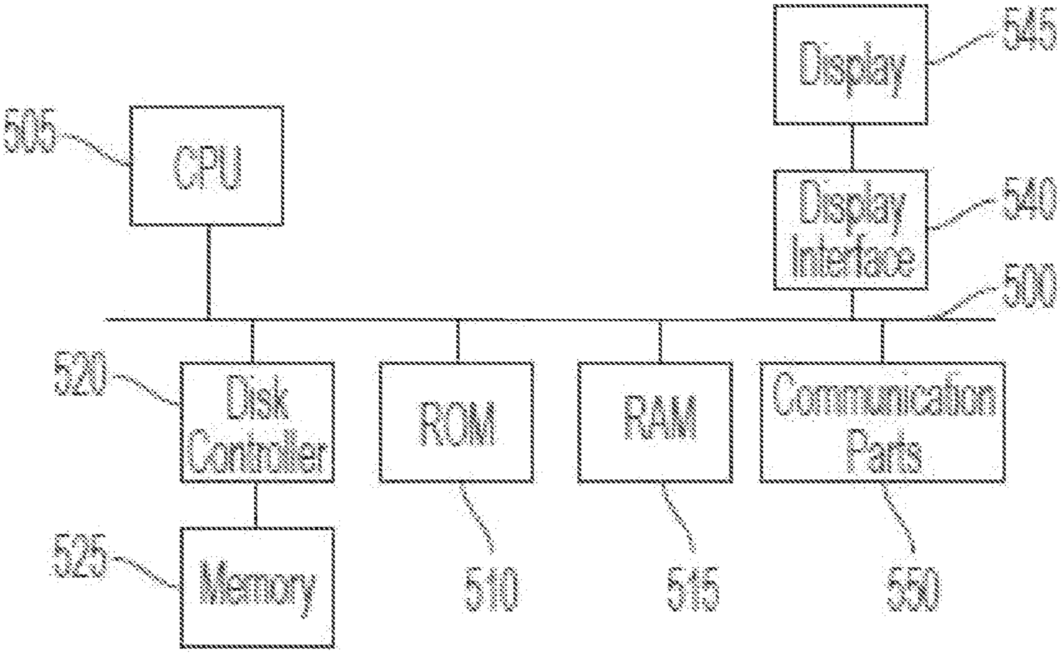
FIG. 7 depicts an example of internal hardware that may be used to implement the various computer processes and systems in accordance with embodiments of the present disclosure.

FIG. 7 depicts an example of internal hardware that may be used to contain or implement the various computer processes and systems as discussed herein. For example, the sensor cap 100 discussed above may include mobile device hardware such as that illustrated in FIG. 7. An electrical bus 500 serves as an information highway interconnecting the other illustrated components of the hardware. The CPU 505 is a central processing unit of the system, performing calculations and logic operations required to execute a program. The CPU 505, alone or in conjunction with one or more of the other elements, is a processing device, computing device or processor as such terms are used within this disclosure. A CPU or "processor" is a component of an electronic device that executes programming instructions.

The term "processor" may refer to either a single processor or to multiple processors that together implement various steps of a process. Unless the context specifically states that a single processor is required or that multiple processors are required, the term "processor" includes both the singular and plural embodiments. Read only memory (ROM) 510 and random access memory (RAM) 515 constitute examples of memory devices, wherein the term "memory device" and similar terms include single device embodiments, multiple devices that together store programming or data, or individual sectors of such devices.

A controller 520 interfaces with one or more optional memory devices 525 that serves as data storage facilities to the system bus 500. These memory devices 525 may include, for example, an external or internal disk drive, a hard drive, flash memory, a USB drive or another type of device that serves as a data storage facility. Such various drives and controllers are optional devices. In some embodiments, the memory devices 525 may be configured to include individual files for storing any software modules or instructions, auxiliary data, incident data, common files for storing groups of contingency tables and/or regression models, or one or more databases for storing the information as discussed above.

The ROM 510 and/or the RAM 515 may store program instructions, software, or interactive modules for performing any of the functional steps associated with the processes as described above. Optionally, program instructions may be stored on a non-transitory, computer readable medium such as a compact disk, a digital disk, flash memory, a memory card, a USB drive, an optical disc storage medium, and/or other recording medium.

In some embodiments, the sensor cap may comprise a display screen or display interface. Such an optional display interface 540 may permit information from the bus 500 to be displayed on the display 545 in audio, visual, graphic or alphanumeric format. For example, analyte conditions measured by the plurality of sensors in the sensor cap may be displayed. Communication with external devices may occur using various communication ports 550. A communication port 550 may be attached to a communications network, such as the Internet, a local area network or a cellular telephone data network.

A first aspect (aspect 1) as described herein provides a sensor cap for a cell culture device comprising: a cylindrical body having a closed end and an open end, wherein the open end is configured to attach to a cell culture device; a sample collection chamber disposed on an interior surface of the cylindrical body; and a plurality of sensors in communication with the sample collection chamber.

A second aspect (aspect 2) as described herein is directed to the sensor cap of aspect 1, wherein the cap comprises a plurality of inductor coils disposed on an exterior surface of the cylindrical body.

A third aspect (aspect 3) as described herein is directed to the sensor cap of aspect 2, wherein each inductor coil of the plurality of inductor coils corresponds to and is in communication with a sensor in the plurality of sensors.

A fourth aspect (aspect 4) as described herein is directed to the sensor cap of aspect 2 or aspect 3, wherein the plurality of inductor coils is concentrically disposed on the closed end of the cap.

A fifth aspect (aspect 5) as described herein is directed to the sensor cap of any of aspects 1-4, wherein the open end comprises threads configured to attach to corresponding threads on a cell culture device.

A sixth aspect (aspect 6) as described herein is directed to the sensor cap of any of aspects 1-5, wherein the exterior of the cap comprises textured regions.

A seventh aspect (aspect 7) as described herein is directed to the sensor cap of any of aspects 1-6, wherein the cap is disposable.

An eighth aspect (aspect 8) as described herein is directed to the sensor cap of any of aspects 1-7, wherein the plurality of sensors is integrated in the body of the sensor cap.

A ninth aspect (aspect 9) as described herein is directed to the sensor cap of any of aspects 1-8, wherein the plurality of sensors is attached to the body of the sensor cap.

A tenth aspect (aspect 10) as described herein is directed to the sensor cap of any of aspects 1-9, wherein the plurality of sensors comprises a dissolved gas sensor, an essential molecule sensor, a cell culture condition sensor, or a combination thereof.

An eleventh aspect (aspect 11) as described herein is directed to the sensor cap of aspect 10, wherein the dissolved gas sensor measures dissolved oxygen or carbon dioxide.

A twelfth aspect (aspect 12) as described herein is directed to the sensor cap of aspect 10, wherein the essential molecule sensor measures sugar, lactic acid, ammonium, salts, vitamins, amino acids, or pyruvate content.

A thirteenth aspect (aspect 13) as described herein is directed to the sensor cap of aspect 12, wherein the sugar content comprises glucose content.

A fourteenth aspect (aspect 14) as described herein is directed to the sensor cap of aspect 10, wherein the cell culture condition sensor measures pH or osmolality.

A fifteenth aspect (aspect 15) as described herein is directed to the sensor cap of any of aspects 1-10, wherein the plurality of sensors comprises inductance-capacitance sensors.

A sixteenth aspect (aspect 16) as described herein is directed to the sensor cap of any of aspects 1-15, wherein the cell culture device comprises a cell culture media bottle, a shaker flask, a cell culture flask, a multilayered cell culture flask, multilayer cell culture vessel, cell culture spinner flask, or a cell culture roller bottle.

A seventeenth aspect (aspect 17) as described herein provides a cell culture media monitoring system configured to non-invasively monitor cell culture media, the system comprising: a cell culture vessel comprising a cell culture chamber, the cell culture chamber having a surface on which cells are cultured; and a sensor cap configured to attach to the cell culture vessel, the sensor cap comprising: a cylindrical body having a closed end and an open end, wherein the open end is configured to attach to a port on the cell culture vessel; a sample collection chamber disposed on an interior surface of the cylindrical body; and a plurality of sensors in communication with the sample collection chamber.

An eighteenth aspect (aspect 18) as described herein is directed to the system of aspect 17, further comprising a controller module configured to control the system.

A nineteenth aspect (aspect 19) as described herein is directed to the system of aspect 17 or aspect 18, further comprising a communications module configured to transfer measurement data from the sensor cap to a data processor.

A twentieth aspect (aspect 20) as described herein is directed to the system of aspect 19, wherein the communications module is configured to communicate through at least one of a wired connection and a wireless connection.

A twenty-first aspect (aspect 21) as described herein is directed to the system of any of aspects 17-20, further comprising a data processing device configured to receive transmitted data collected by the sensor cap.

A twenty-second aspect (aspect 22) as described herein provides a method of measuring cell culture media conditions comprising: attaching a sensor cap to a cell culture device, wherein the cell culture device comprises a cell culture surface for culturing cells and a volume of cell culture media; tilting the cell culture device to flow cell culture media to the sensor cap, wherein a sample of the cell culture media is collected in a sample collection chamber in the sensor cap; and measuring cell culture media conditions of the sample via a plurality of sensors in the sensor cap.

A twenty-third aspect (aspect 23) as described herein is directed to the method of aspect 22, wherein the sample is collected from an area other than the cell culture surface.

A twenty-fourth aspect (aspect 24) as described herein is directed to the method of aspect 22 or aspect 23, wherein the plurality of sensors measures dissolved gases, essential molecules, cell culture conditions, or a combination thereof.

A twenty-fifth aspect (aspect 25) as described herein is directed to the method of any of aspects 22-24, further comprising transmitting data collected by the sensor cap during the measurement step to a data processing device.

A twenty-sixth aspect (aspect 26) as described herein is directed to the method of aspect 25, further comprising monitoring cell culture media conditions in the cell culture device by analyzing the collected data.

A twenty-seventh aspect (aspect 27) as described herein is directed to the method of aspect 25, wherein the data is transmitted through noninvasive wireless reading of inductor coils on an exterior surface of the sensor cap.

A twenty-eighth aspect (aspect 28) as described herein is directed to the method of aspect 27, wherein the noninvasive wireless reading is through a microcontroller board.

A twenty-ninth aspect (aspect 29) as described herein is directed to the method of aspect 27, wherein the noninvasive wireless reading is through a radio frequency identification (RFID) chip.

A thirtieth aspect (aspect 30) as described herein is directed to the method of aspect 22, further comprising providing an output of the measured data collected by the sensor cap.

It will be appreciated that the various disclosed embodiments can involve particular features, elements or steps that are described in connection with that particular embodiment. It will also be appreciated that a particular feature, element or step, although described in relation to one particular embodiment, can be interchanged or combined with alternate embodiments in various non-illustrated combinations or permutations.

It is to be understood that, as used herein the terms “the,” “a,” or “an,” mean “at least one,” and should not be limited to “only one” unless explicitly indicated to the contrary. Thus, for example, reference to “a component” includes embodiments having two or more such components unless the context clearly indicates otherwise.

Ranges can be expressed herein as from “about” one particular value, and/or to “about” another particular value. When such a range is expressed, embodiments include from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments can be disclosed using the transitional phrase “comprising,” it is to be understood that alternative embodiments, including those that can be described using the transitional phrases “consisting” or “consisting essentially of,” are implied. Thus, for example, implied alternative embodiments to an apparatus that comprises A+B+C include embodiments where an apparatus consists of A+B+C and embodiments where an apparatus consists essentially of A+B+C.

It will be apparent to those skilled in the art that various modifications and variations can be made to the present disclosure without departing from the spirit and scope of the disclosure. Thus, it is intended that the present disclosure cover the modifications and variations of this disclosure provided they come within the scope of the appended claims and their equivalents.

What is claimed is:

1. A sensor cap for a cell culture device comprising:
- a cylindrical body having a closed end and an open end, wherein the open end is configured to attach to a cell culture device;
- a sample collection chamber disposed on an interior surface of the cylindrical body;
- a plurality of sensors in communication with the sample collection chamber; and
- a plurality of inductor coils disposed on an exterior surface of the cylindrical body.

2. The sensor cap of claim 1, wherein each inductor coil corresponds to and is in communication with a sensor in the plurality of sensors.

3. The sensor cap of claim 1, wherein the plurality of inductor coils is concentrically disposed on the closed end of the cap.

4. The sensor cap of claim 1, wherein the open end comprises threads configured to attach to corresponding threads on a cell culture device.

5. The sensor cap of claim 1, wherein the exterior of the cap comprises textured regions.

6. The sensor cap of claim 1, wherein the cap is disposable.

7. The sensor cap of claim 1, wherein the plurality of sensors is integrated in the body of the sensor cap.

8. The sensor cap of claim 1, wherein the plurality of sensors is attached to the body of the sensor cap.

9. The sensor cap of claim 1, wherein the plurality of sensors comprises a dissolved gas sensor, an essential molecule sensor, a cell culture condition sensor, or a combination thereof.

10. The sensor cap of claim 9, wherein the dissolved gas sensor measures dissolved oxygen or carbon dioxide.

11. The sensor cap of claim 9, wherein the essential molecule sensor measures sugar, lactic acid, ammonium, salts, vitamins, amino acids, or pyruvate content.

12. The sensor cap of claim 11, wherein the sugar content comprises glucose content.

13. The sensor cap of claim 9, wherein the cell culture condition sensor measures pH or osmolality.

14. The sensor cap of claim 1, wherein the plurality of sensors comprises inductance-capacitance sensors.

15. The sensor cap of claim 1, wherein the cell culture device comprises a cell culture media bottle, a shaker flask, a cell culture flask, a multilayered cell culture flask, multi-layer cell culture vessel, cell culture spinner flask, or a cell culture roller bottle.

16. A cell culture media monitoring system configured to non-invasively monitor cell culture media, the system comprising:

a cell culture vessel comprising a cell culture chamber, the cell culture chamber having a surface on which cells are cultured; and a sensor cap configured to attach to the cell culture vessel, the sensor cap comprising:

a cylindrical body having a closed end and an open end, wherein the open end is configured to attach to a port on the cell culture vessel;

a sample collection chamber disposed on an interior surface of the cylindrical body;

a plurality of sensors in communication with the sample collection chamber; and a plurality of inductor coils disposed on an exterior surface of the cylindrical body.

17. The system of claim 16, further comprising a controller module configured to control the system.

18. The system of claim 16, further comprising a communications module configured to transfer measurement data from the sensor cap to a data processor.

19. The system of claim 18, wherein the communications module is configured to communicate through noninvasive wireless reading of the inductor coils at least one of a wired connection and a wireless connection.

20. The system of claim 16, further comprising a data processing device configured to receive transmitted data collected by the sensor cap.

21. A method of measuring cell culture media conditions comprising:

attaching an open end of a sensor cap to a cell culture device, wherein the cell culture device comprises a cell culture surface for culturing cells and a volume of cell culture media, and wherein the sensor cap comprises:

a cylindrical body having a closed end and the open end;

a sample collection chamber disposed on an interior surface of the cylindrical body;

a plurality of sensors in communication with the sample collection chamber; and a plurality of inductor coils disposed on an exterior surface of the cylindrical body;

tilting the cell culture device to flow cell culture media to the sensor cap, wherein a sample of the cell culture media is collected in the sample collection chamber in the sensor cap; and measuring cell culture media conditions of the sample via the plurality of sensors of the sensor cap.

22. The method of claim 21, wherein the sample is collected from an area other than the cell culture surface.

23. The method of claim 21, wherein the plurality of sensors measures dissolved gases, essential molecules, cell culture conditions, or a combination thereof.

24. The method of claim 21, further comprising transmitting data collected by the sensor cap during the measurement step to a data processing device.

25. The method of claim 24, further comprising monitoring cell culture media conditions in the cell culture device by analyzing the collected data.

26. The method of claim 24, wherein the data is transmitted through noninvasive wireless reading of the inductor coils.

27. The method of claim 21, further comprising providing an output of the measured data collected by the sensor cap.

* * * * *